(12) United States Patent
Seed et al.

(10) Patent No.: US 8,440,655 B2
(45) Date of Patent: May 14, 2013

(54) COMBINATION THERAPY FOR THE TREATMENT OF DIABETES

(75) Inventors: Brian Seed, Boston, MA (US); Jordan Mechanic, Sunnyvale, CA (US)

(73) Assignee: Theracos, Inc., Marlborough, MA (US)

( * ) Notice: Subject to any disclaimer, the term of this patent is extended or adjusted under 35 U.S.C. 154(b) by 147 days.

(21) Appl. No.: 13/165,549

(22) Filed: Jun. 21, 2011

(65) Prior Publication Data

US 2011/0312946 A1 Dec. 22, 2011

Related U.S. Application Data

(60) Provisional application No. 61/356,779, filed on Jun. 21, 2010.

(51) Int. Cl.
*A61K 31/55* (2006.01)

(52) U.S. Cl.
USPC .......................................................... 514/220

(58) Field of Classification Search .................. 514/220
See application file for complete search history.

(56) References Cited

U.S. PATENT DOCUMENTS

| | | | |
|---|---|---|---|
| 3,953,430 A | 4/1976 | Safir | |
| 4,168,269 A | 9/1979 | Brabander et al. | |
| 4,172,831 A | 10/1979 | Chakrabarti et al. | |
| 4,381,301 A | 4/1983 | Rainer | |
| 4,536,518 A | 8/1985 | Welch, Jr. et al. | |
| 5,140,025 A | 8/1992 | Grundler et al. | |
| 5,324,832 A | 6/1994 | Jacobson et al. | |
| 5,344,832 A | 9/1994 | Cincotta et al. | |
| 5,585,347 A | 12/1996 | Meier et al. | |
| 5,668,155 A | 9/1997 | Cincotta et al. | |
| 5,700,795 A | 12/1997 | Cincotta et al. | |
| 5,712,265 A | 1/1998 | Cincotta et al. | |
| 5,795,895 A | 8/1998 | Anchors | |
| 6,803,357 B1 | 10/2004 | Bachovchin et al. | |
| 7,109,198 B2 | 9/2006 | Gadde et al. | |
| 7,544,684 B2 * | 6/2009 | Eggenweiler et al. | 514/241 |
| 2002/0137787 A1 | 9/2002 | Geho et al. | |
| 2004/0204472 A1 | 10/2004 | Briggs et al. | |
| 2005/0227998 A1 | 10/2005 | Voelker | |
| 2007/0293481 A1 | 12/2007 | Seed et al. | |
| 2010/0021555 A1 | 1/2010 | Geiginger et al. | |

FOREIGN PATENT DOCUMENTS

| | | |
|---|---|---|
| WO | WO 95/35110 | 12/1995 |
| WO | WO 2005/051297 A2 | 6/2005 |
| WO | WO 2006/127418 A1 | 11/2006 |
| WO | WO 2008/083200 A2 | 7/2008 |

OTHER PUBLICATIONS

Mancini et al., "Pharmacological treatment of obesity," Arq Bras Endocrinol Metabol., 2006, vol. 50, No. 2, pp. 377-389.
Appolinario, et al., "Psychotropic Drugs in Treatment of Obesity," *CNS Drugs* (2004) 18(10):629-51.
Faber and Binder et al., Diabetes Metab., 1986, Rev. 2:331-345.
Greenway, et al., "Rational Design of a Combination Medication for the Treatment of Obesity," *Obesity*, (Silver Spring), Jan. 2009;17(1):30-9.
Grundy et al., Circulation, 2004, 109:433-438.
Longdong, et al., "Telenzepine is at Least 25 Times More Potent Than Pirenzepine—A Dose Response and Comparative Secretory Study in Man," 28 GUT 888 (1987).
Jia, et al., "Mechanism of Drug Combinations: Interaction and Network Perspectives," *Nature Reviews—Drug Discovery* (2009) 8:111-128.
Korner et al., "Pharmacological Approaches to Weight Reduction: Therapeutic Targets," *J. Clin. Endocrinol. Metab.*, 2004 89: 2616-2621.
Li et al., "Meta-Analysis: Pharmacologic Treatment of Obesity," *Ann. Intern. Med.* 2005:142:532-546.
Muratori, F., et al., "Accute Cholinergic Blockade with Pirenzepine Reduces the Insulin and Glucose Responses to Oral Glucose Test in Obese Women," *International Journal of Obesity*, Newman Pub., London, GB, vol. 28, No. Suppl. 1, Apr. 1, 2004, p. S221.
Sansone, et al., "Naturalistic Study of the Weight Effects of Amitriptyline, Fluoxetine, and Sertraline in an Outpaient Medical Setting," *J Clinical Psychopharmacol* (2000) 20(2): 272-4.
Valentino et al., "Central and Peripheral Molecular Targets for Antiobesity Pharmacotherapy," *Nature Publishing*, vol. 87, No. 6, Jun. 2010, 652-662.
Wadden, et al., "Sertraline and Relapse Prevention Training Following Treatment by Very-Low-Calorie Diet: A Controlled Clinical Trial," *Obesity Res* (1995) 3(6):549-557.
Zangeneh et al., Endocrine Practice, 2006, 12:388-393.
International Search Report and Written Opinion, PCT application No. PCT/US11/41252, dated Oct. 31, 2011, 9 pages.

* cited by examiner

*Primary Examiner* — Rei-tsang Shiao
(74) *Attorney, Agent, or Firm* — Kilpatrick Townsend & Stockton LLP

(57) ABSTRACT

The present invention provides methods of treating, reducing, preventing, or inhibiting symptoms of diabetes and/or lowering plasma levels of HbA1c by co-administration of therapeutic or subtherapeutic doses of telenzepine and sertraline to a subject in need thereof.

36 Claims, No Drawings

COMBINATION THERAPY FOR THE TREATMENT OF DIABETES

CROSS-REFERENCE TO RELATED APPLICATIONS

This application claims the benefit of U.S. Provisional Application No. 61/356,779 filed Jun. 21, 2010, the content of which is incorporated herein by reference in its entirety.

FIELD OF THE INVENTION

The present invention provides methods for treating diabetes and associated complications by co-administration of sertraline and telenzepine.

BACKGROUND OF THE INVENTION

In 2003, the International Diabetes Foundation estimated that there were 194 million people worldwide with diabetes mellitus. It further estimated that another 314 million people worldwide had impaired glucose tolerance or "pre-diabetes," a condition that often precedes diabetes. Both of these figures are expected to rise significantly by the year 2025. In the United States alone, it is estimated that 23.6 million children and adults—nearly 8% of the country's population—have diabetes, while another 57 million people have pre-diabetes.

Diabetes mellitus ("diabetes") is one of the leading causes of premature illness and death in most countries, due in part to the increased risk of cardiovascular disease that is associated with diabetes. Diabetes is also among the leading causes of kidney failure, blindness, visual disability, and non-traumatic amputation of the lower limbs. The chronic nature of diabetes also makes it a costly disease. In 2007, it was estimated that in the United States, the total costs of diagnosed diabetes, including direct medical costs and indirect costs due to disability, work loss, and premature mortality, totaled $174 billion.

Currently, diabetes is generally treated using one or a combination of medications including sulfonylureas, meglitinides, biguanides, thiazolidinediones, alpha-glucosidase inhibitors, and DPP-4 inhibitors. However, existing diabetes medications are associated with various disadvantages such as side effects, short half-life, and/or negative interactions with other drugs.

Thus, there exists a need for new and effective medications and/or combinations of medications for the treatment of diabetes. The present invention addresses this and other needs.

BRIEF SUMMARY OF THE INVENTION

The present invention provides methods of treating, reducing, alleviating, inhibiting, delaying onset of and/or preventing the causes and/or symptoms of diabetic conditions and associated complications by administration of telenzepine in combination with sertraline to a patient in need thereof.

Accordingly, in one aspect, the present invention provides methods of treating a diabetic condition (e.g., diabetes, metabolic syndrome, pre-diabetes, or hyperglycemia) in a subject in need thereof, said method comprising co-administering to the subject telenzepine and sertraline.

In a further aspect, the invention provides methods of lowering blood, plasma or serum levels of HbA1c in a subject in need thereof, wherein the subject is diabetic, non-diabetic, or pre-diabetic, comprising co-administering to the subject telenzepine and sertraline. In some embodiments, the blood, plasma or serum levels of HbA1c are lowered to below a predetermined threshold level, e.g., to below 13%, 12%, 11%, 10%, 9%, 8%, 7%, 6.5%, 6%, 5.5% or 5% of the total hemoglobin after co-administration of telenzepine and sertraline. In some embodiments, the blood, plasma or serum levels of HbA1c are reduced by at least about 5%, 10%, 15%, 20%, 25%, 30%, 40%, 50%, 60%, 70%, 80%, 90%, 100% or more, after co-administration of telenzepine and sertraline, e.g., in comparison to an earlier reference time point or in comparison to the blood, plasma or serum levels of HbA1c prior to co-administration of telenzepine and sertraline.

In yet another aspect, the present invention provides for a combination of telenzepine and sertraline for use in the treatment of a diabetic condition (e.g., diabetes, metabolic syndrome, pre-diabetes, or hyperglycemia).

In some embodiments, one or both of the telenzepine and sertraline are administered in a therapeutically effective amount. In some embodiments, one or both of the telenzepine and sertraline are administered in a sub-therapeutic amount. In some embodiments, the telenzepine is administered at a dose in the range of about 0.1-10 mg/day, for example, about 0.1-10 mg/day, about 0.2-8 mg/day, about 0.3-6 mg/day, about 0.5-5 mg/day, about 0.7-4 mg/day, or about 1-3 mg/day. In some embodiments, the telenzepine is administered at a dose of about 0.1 mg/day, about 0.2 mg/day, about 0.3 mg/day, about 0.4 mg/day, about 0.5 mg/day, about 0.6 mg/day, about 0.7 mg/day, about 0.8 mg/day, about 0.9 mg/day, about 1 mg/day, about 1.5 mg/day, about 2 mg/day, about 2.5 mg/day, about 3 mg/day, about 3.5 mg/day, about 4 mg/day, about 4.5 mg/day, about 5 mg/day, about 5.5 mg/day, or about 6 mg/day. In some embodiments, the sertraline is administered at a dose in the range of about 25-250 mg/day, for example, about 50-250 mg/day, about 50-200 mg/day, or about 50-150 mg/day. In some embodiments, the sertraline is administered at a dose of about 25 mg/day, about 50 mg/day, about 75 mg/day, about 100 mg/day, about 125 mg/day, about 150 mg/day, about 175 mg/day, or about 200 mg/day.

In some embodiments, the telenzepine and sertraline are co-administered over a time period of at least about 20, 40, 60, 80 or 100 days, for example, at least 150, 200, 250, 300, 350, 400, 450, 500, 550, 600, 650, 700, 800, 900, or 1000 days, for example, at least 1 year, 2 years, 3 years, 4 years, or longer, as appropriate.

In some embodiments, the telenzepine is systemically administered. In some embodiments, one or both of the telenzepine and the sertraline are administered in a sustained release formulation. In some embodiments, the telenzepine and the sertraline are administered concurrently. In some embodiments, the telenzepine and the sertraline are administered sequentially.

In some embodiments, the method (e.g., the method of treating diabetes in a subject or the method of lowering blood, plasma or serum levels of HbA1c in a subject) as described herein further comprises administering to the subject one or more anti-diabetic agents and/or agents for treating diabetic complications. In some embodiments, the combination of telenzepine and sertraline for use in the treatment of diabetes further comprises one or more anti-diabetic agents and/or agents for treating diabetic complications.

In some embodiments, the subject is pre-diabetic. In some embodiments, the subject has type 2 diabetes. In some embodiments, the subject has metabolic syndrome. In some embodiments, the subject is not overweight or obese. In some embodiments, the subject is a human.

DEFINITIONS

The term "diabetes" refers to a disease or condition that is generally characterized by metabolic defects in production and utilization of glucose which result in the failure to maintain appropriate blood sugar levels in the body. A subject is identified as having diabetes if the subject has a fasting blood glucose level greater than 125 mg/dl, a 2 hour post-load glucose reading of greater than 200 mg/dl, or a HbA1c level greater than or equal to 6.5%.

The term "pre-diabetes" refers to a disease or condition that is generally characterized by impaired glucose tolerance and which frequently precedes the onset of diabetes in a subject.

A subject is identified as having pre-diabetes if the subject has a fasting blood glucose level greater than 100 mg/dl but less than or equal to 125 mg/dl, a 2 hour post-load glucose reading of greater than 140 mg/dl but less than 200 mg/dl, or a HbA1c level greater than or equal to 6.0% but less than 6.5%.

The term "metabolic syndrome" refers to a group of metabolic risk factors for cardiovascular disease and type 2 diabetes. Metabolic syndrome is also known as "metabolic syndrome X" or "syndrome X." The metabolic risk factors include excess intra-abdominal fat, insulin resistance (generally characterized by impaired fasting glucose, impaired glucose tolerance, or type 2 diabetes), atherogenic dyslipidemia (typically manifested by elevated plasma triglyceride levels and decreased high density lipoprotein (HDL) cholesterol level), hypertension, proinflammatory state (characterized by elevated levels of C-reactive protein (CRP), and prothrombotic state (characterized by increased plasma plasminogen activator inhibitor (PAI)-1 and fibrinogen). A subject is identified as having metabolic syndrome if the subject has insulin resistance and at least two other risk factors.

The term "hyperglycemia" refers to elevated blood glucose levels in the body, which results from metabolic defects in production and utilization of glucose. A subject is identified as hyperglycemic if the subject has a fasting blood glucose level that consistently exceeds 126 mg/dl.

The term "diabetic condition" refers to a condition characterized by impaired glucose production and/or utilization and includes diabetes (e.g., type 1 diabetes, type 2 diabetes, and gestational diabetes), pre-diabetes, metabolic syndrome, hyperglycemia, impaired glucose tolerance, and impaired fasting glucose.

The term "obese" or "obesity" refers to an individual who has a body mass index (BMI) of 30 kg/m$^2$ or more due to excess adipose tissue. Obesity also can be defined on the basis of body fat content: greater than 25% body fat content for a male or more than 30% body fat content for a female. A "morbidly obese" individual has a body mass index greater than 35 kg/m$^2$.

The term "overweight" refers to an individual who has a body mass index of 25 kg/m$^2$ or more, but less than 30 kg/m$^2$.

The term "body mass index" or "BMI" refers to a weight to height ratio measurement that estimates whether an individual's weight is appropriate for their height. As used herein, an individual's body mass index is calculated as follows:

$$BMI=(pounds \times 700)/(height\ in\ inches)^2$$

or $$BMI=(kilograms)/(height\ in\ meters)^2$$

The term "baseline body weight" refers to the body weight presented by the individual at the initiation of treatment.

As used herein, "administering" means oral ("po") administration, administration as a suppository, topical contact, intravenous ("iv"), intraperitoneal ("ip"), intramuscular ("im"), intralesional, intranasal or subcutaneous ("sc") administration, or the implantation of a slow-release device e.g., a mini-osmotic pump, to a subject. Administration is by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration, with the proviso that, as used herein, systemic administration does not include direct administration to the brain region by means other than via the circulatory system, such as intrathecal injection and intracranial administration.

The term "therapeutically effective amount" refers to that amount of the compound being administered sufficient to prevent or decrease the development of one or more of the symptoms of the disease, condition or disorder being treated.

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-convulsant, anti-depressant, anti-inflammatory, anti-hypertensive, cardioprotective, or organ protective effects), or that quantitatively is less than the established therapeutic dose for that particular pharmacological agent (e.g., as published in a reference consulted by a person of skill, for example, doses for a pharmacological agent published in the Physicians' Desk Reference, 62nd Ed., 2008, Thomson Healthcare or Brunton, et al., Goodman & Gilman's The Pharmacological Basis of Therapeutics, 11th edition, 2006, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The term "co-administer" refers to the simultaneous presence of two active agents in the blood of an individual. Active agents that are co-administered can be concurrently or sequentially delivered.

As used herein, the terms "treating" and "treatment" refer to delaying the onset of, retarding or reversing the progress of, or alleviating or preventing either the disease or condition to which the term applies, or one or more symptoms of such disease or condition.

The terms "reduce," "inhibit," "relieve," and "alleviate" refer to the detectable decrease in symptoms of diabetes, as determined by a trained clinical observer. A reduction in diabetic symptoms can be measured using any test known in the art, including but not limited to, decreased blood or plasma glucose levels, decreased glycosylated hemoglobin levels, increased blood or plasma insulin levels, increased C-peptide levels, and increased beta cell function.

The terms "patient," "subject" or "individual" interchangeably refer to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster, guinea pig).

As used herein, the terms "selective muscarinic receptor $M_1$ antagonist" and "$M_1R$-selective antagonist" refer to a muscarinic acetylcholine receptor antagonist that exhibits preferential interaction with the muscarinic receptor $M_1$ subtype in comparison to the muscarinic receptor subtypes $M_2$ and $M_3$. Exemplified $M_1R$-selective antagonists include, but are not limited to, telenzepine and pirenzepine. Preferential binding need not be complete. For example, despite comparable affinities for $M_1$ and $M_4$ receptor subtypes, the muscarinic receptor antagonist pirenzepine is classified as an $M_1R$-selective antagonist.

Preferential binding of a $M_1R$-selective antagonist can be measured in a competitive displacement assay. A $M_1R$-selective antagonist will preferentially displace a known $M_1R$-selective ligand (e.g., telenzepine) in comparison to known $M_2$ (e.g., tripitramine, himbacine, methoctramine) and $M_3$ (e.g., darifenacin, hexahydrosiladiphenidol) selective ligands. Alternatively, a $M_1R$-selective antagonist will preferentially displace a nonselective muscarinic ligand (e.g., quinuclidinyl benzilate (QNB), N-methylscopolamine (NMS)) from an $M_1$ receptor subtype in comparison to displacing the non-selective muscarinic ligand from binding to the $M_2$ and $M_3$ receptor subtypes. The relative potencies for displacement of radiolabeled competitors can be expressed in terms of the concentration at which 50% of the competitor is displaced ($IC_{50}$), or in terms of an equilibrium dissociation constant ($K_d$). The $IC_{50}$ value and/or the equilibrium dissociation constant can be calculated using available software by entering the values of detected labeled ligand in the presence of titrated amounts of unlabeled test compound (e.g., LIGAND (Munson, P. J., and Rodbard, D., *Anal. Biochem.* (1980) 107:220-39 or DATAPLOT, National Technical Information Services). A $M_1R$-selective antagonist will have an $IC_{50}$ value or a $K_d$ value for binding to an $M_1$ receptor subtype that is at least about 3-fold less, preferably at least about 10-fold less, and more preferably at least about 30-fold less than its $IC_{50}$ value or $K_d$ value for binding to $M_2$ and $M_3$ receptor subtypes. Applicable radioligand binding assays, using radiolabeled NMS or QNB, are disclosed in Buckley, et al., *Molecular Pharmacology* (1989) 35:469-76 and Bolden, et al, *J Pharmacol Exp Ther.* (1992) 260:576-80.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than a $M_1R$-selective antagonist and an antidepressant. In some embodiments, the phrase "consisting essentially of" expressly excludes the inclusion of one or more additional active agents other than telenzepine and sertraline.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21$^{st}$ Ed., Lippencott Williams & Wilkins (2006). As discussed therein, immediate and nonimmediate release can be defined kinetically by reference to the following equation:

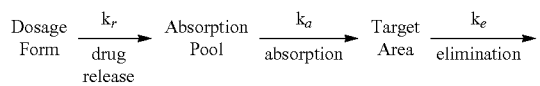

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

DETAILED DESCRIPTION

I. Introduction

The present invention is based, in part, on the surprising discovery that the combined administration of telenzepine and sertraline is useful in reducing, treating, ameliorating, and/or preventing symptoms of diabetes. By co-administering to a subject in need thereof a therapeutic or subtherapeutic dose of each of telenzepine and sertraline, the symptoms of diabetes can be treated, ameliorated and/or improved. Additionally, with administration of therapeutic or prophylactic regimes of telenzepine and sertraline, markers that are indicative of diabetic conditions, such as blood glucose levels, HbA1c levels, and C-peptide levels can be modulated to indicate amelioration or reduction of disease symptoms. By co-administering to a subject in need thereof a therapeutic or subtherapeutic dose of each of telenzepine and sertraline, blood levels of glucose and/or HbA1c (glycosylated hemoglobin) can be reduced to below threshold levels, and C-peptide levels in the blood can be maintained or increased to above threshold levels.

A further advantage of the present invention is that co-administration of a therapeutic or subtherapeutic dose of each of telenzepine and sertraline to a subject in need thereof can ameliorate, reduce, relieve, or prevent secondary conditions or symptoms that result as a complication from diabetes. Therefore, the methods of treatment of the present invention can reduce hypertension, reduce the risk for cardiovascular disease, retinopathy, nephropathy, and neuropathy, and/or promote weight loss or maintenance of a stable weight.

II. Methods of Treating Diabetic Conditions

A. Conditions Subject to Treatment

The present methods and compositions find use in the treatment and prevention of diabetic conditions in subjects in need thereof. Diabetic conditions include, for example, type 1 diabetes, type 2 diabetes, gestational diabetes, pre-diabetes, hyperglycemia, and metabolic syndrome. For the purposes of treatment, the subject may have diabetes, e.g., type 2 diabetes. For the purposes of prevention, the subject may be at risk of developing diabetes or be pre-diabetic. In some embodiments, the subject has metabolic syndrome.

Diabetes mellitus (generally referred to herein as "diabetes") is a disease that is characterized by impaired glucose regulation. Diabetes is a chronic disease that occurs when the pancreas fails to produce enough insulin or when the body cannot effectively use the insulin that is produced, resulting in an increased concentration of glucose in the blood (hyperglycemia). Diabetes may be classified as type 1 diabetes (previously known as insulin-dependent, juvenile, or childhood-onset diabetes), type 2 diabetes (previously known as non-insulin-dependent or adult-onset diabetes), or gestational diabetes. Additionally, intermediate conditions such as impaired glucose tolerance and impaired fasting glycemia are recognized as conditions that indicate a high risk of progressing to type 2 diabetes.

In type 1 diabetes, insulin production is absent due to autoimmune destruction of pancreatic β-cells. There are several markers of this autoimmune destruction, detectable in body fluids and tissues, including islet cell autoantibodies, insulin autoantibodies, glutamic acid decarboxylase autoantibodies, and tyrosine phosphatase ICA512/IA-2 autoantibodies. The pathogenesis of β-cell destruction involves interactions between susceptibility genes, autoantigens, and environmental factors, although these interactions are not completely understood.

In type 2 diabetes, which is estimated by the World Health Organization to comprise 90% of people with diabetes around the world, insulin secretion may be inadequate, or peripheral insulin resistance (the decreased biological response to normal concentrations of circulating insulin) and increased hepatic production of glucose make the existing insulin levels in the body inadequate to normalize plasma glucose levels. It is believed that insulin resistance is the primary defect, preceding the defect in insulin secretion, although the hyperglycemia that develops when insulin secretion cannot compensate for insulin resistance may itself impair insulin secretion by desensitizing β-cells and/or causing β-cell dysfunction. The pathogenesis of type 2 diabetes is believed to result from a combination of genetic factors and environmental factors such as diet and exercise. For example, type 2 diabetes is commonly, although not always, associated with obesity, and obesity causes insulin resistance in many patients, although the mechanism by which it does so is not clear.

Besides type 1 and type 2 diabetes, diabetes is more rarely caused by any of a number of other conditions, including pregnancy, pancreatic diseases, endocrinopathies, toxins, and drug-induced diabetes. The methods of the present invention can be used with regard to any form of diabetes.

Type 2 diabetes is often preceded by pre-diabetes, in which blood glucose levels are higher than normal but not yet high enough to be diagnosed as diabetes. The term "pre-diabetes," as used herein, is interchangeable with the terms "Impaired Glucose Tolerance" or "Impaired Fasting Glucose," which are terms that refer to tests used to measure blood glucose levels. Individuals may be pre-diabetic for several years or a decade or more before developing type 2 diabetes, although not all individuals who are pre-diabetic eventually develop diabetes. Although pre-diabetes often has no overt signs or symptoms, it is believed that long-term damage to the body, particularly to the heart and circulatory system, occurs during pre-diabetes.

Early symptoms of diabetes are the symptoms of hyperglycemia, including osmotic diuresis caused by glycosuria (excretion of glucose by the kidneys), leading to urinary frequency, polyuria, polydipsia, and severe dehydration; weight loss, nausea, and vomiting; and blurred vision. However, patients with hyperglycemia are often asymptomatic.

Chronic hyperglycemia in diabetes is associated with multiple, primarily vascular complications affecting microvasculature and/or macrovasculature. These long-term complications include retinopathy (leading to focal blurring, retinal detachment, and partial or total loss of vision), nephropathy (leading to renal failure), neuropathy (leading to pain, numbness, and loss of sensation in limbs, and potentially resulting in foot ulceration and/or amputation), cardiomyopathy (leading to heart failure), and increased risk of infection.

Metabolic syndrome is a cluster of metabolic risk factors including excess intra-abdominal fat, insulin resistance, atherogenic dyslipidemia, hypertension, proinflammatory state, and prothrombotic state. The pathogenesis of metabolic syndrome is mainly due to abdominal obesity and insulin resistance, although other factors have also been implicated as contributors to metabolic syndrome. The World Health Organization guidelines define metabolic syndrome as insulin resistance with at least two other risk factors additionally present, although there are at least two other sets of clinical criteria for diagnosing metabolic syndrome that are similar but distinct from the criteria set forth by the World Health Organization (reviewed in Grundy et al., *Circulation* 109: 433-438 (2004)); according to these guidelines, an individual is identified as having insulin resistance if the individual has type 2 diabetes, has impaired fasting glucose, or has impaired glucose tolerance, or if the individual has normal fasting glucose levels, has glucose uptake below the lowest quartile for the background population under investigation under hyperinsulinemic or euglycemic conditions. The primary clinical outcome of metabolic syndrome is cardiovascular disease, although most people with metabolic syndrome are at increased risk for type 2 diabetes and other conditions such as cholesterol gallstones, fatty liver, polycystic ovary syndrome, and some forms of cancer.

Diabetic conditions that are subject to treatment according to the methods of the present invention can be diagnosed or monitored using any of a number of assays known in the field. Examples of assays for diagnosing or categorizing an individual as diabetic or pre-diabetic or monitoring said individual include, but are not limited to, a glycosylated hemoglobin (HbA1c) test, a connecting peptide (C-peptide) test, a fasting plasma glucose (FPG) test, an oral glucose tolerance test (OGTT), and a casual plasma glucose test.

HbA1c is a biomarker that measures the amount of glycosylated hemoglobin in the blood. HbA1c designates a stable minor glycated sub fraction of hemoglobin. It is a reflection of the mean blood glucose levels during the last 6-8 weeks, and is expressed in percent (%) of total hemoglobin. HbA1c is a measure of chronic glycemic levels over a period of 2-3 months, and in contrast to other tests such as FPG and OGTT, it is not affected by short-term lifestyle changes (e.g., changes to diet or exercise of a period of a few days or weeks). Therefore, the HbA1c is a test that indicates how well diabetes has been controlled over the course of several months. A patient is classified as diabetic and is subject to treatment according to the methods of the present invention if the patient has an HbA1c level of greater than or equal to 6.5%, although an initial diagnosis of diabetes should be confirmed using FPG or OGTT unless there are unequivocal symptoms of diabetes, or unless the first HbA1c test is greater than or equal to 7.0%, in which case the diagnosis can be confirmed by a second HbA1c test of greater than or equal to 6.5%. A patient is classified as pre-diabetic and is subject to treatment according to the methods of the present invention if the patient has a HbA1c level that is greater than or equal to 6.0% but less than 6.5%. The closer a diabetic or pre-diabetic patient's HbA1c level is to 6%, the better the patient's control of diabetes. For every 30 mg/dl increase in A1c blood glucose, there is a 1% increase in HbA1c, and the risk of complications increases.

Alternatively, diabetes or pre-diabetes can be diagnosed by measuring blood glucose levels using any of several known tests in the field, including a fasting plasma glucose test or an oral glucose tolerance test. Using the fasting plasma glucose (FPG) test, in which a patient's blood glucose level is measured following a period of fasting, a patient is classified as diabetic and is subject to treatment according to the methods of the present invention if the patient has a threshold FPG greater than 125 mg/dl. Using the FPG test, a patient is classified as pre-diabetic and is subject to treatment according to the methods of the present invention if the patient has a threshold FPG greater than 100 mg/dl but less than or equal to 125 mg/dl. Using the oral glucose tolerance test (OGTT), in which a patient's blood glucose level is measured two hours after a glucose challenge to the body, a patient is classified as diabetic and is subject to treatment according to the methods of the present invention if the patient has a threshold 2-hour OGTT glucose level greater than 200 mg/dl. A patient is classified as pre-diabetic and is subject to treatment according to the methods of the present invention if the patient has a threshold 2-hour OGTT glucose level greater than 140 mg/dl but less than 200 mg/dl.

C-peptide, which like insulin is produced from proinsulin molecules, is secreted from islet cells into the bloodstream in equimolar proportion as insulin, and is used a biomarker for β-cell function and insulin secretion. See Faber and Binder, *Diabetes Metab. Rev.* 2:331-345 (1986). Although not all individuals with pre-diabetes or type 2 diabetes have impaired insulin secretion, many diabetic individuals do have defects in insulin production, and it has been reported that a gradual reduction in insulin secretion is characteristic of type 2 diabetes (Zangeneh et al., *Endocrine Practice* 12:388-393 (2006)). Therefore, C-peptide levels measure another aspect of diabetic conditions. A fasting C-peptide measurement that is between 0.5-2.0 ng/ml is considered to be "normal" (e.g., non-diabetic). A fasting C-peptide measurement greater than 2.0 ng/ml is indicative of high levels of insulin, while a fasting C-peptide measurement less than 0.5 ng/ml indicates insufficient insulin production.

A subject who has been classified as having a diabetic condition, and who is subject to treatment according to the methods of the present invention, may be monitored for efficacy of treatment by measuring any of the biomarkers and/or blood glucose indicators described herein, including but not limited to, glycosylated hemoglobin levels, C-peptide levels, fasting plasma glucose levels, and oral glucose tolerance test (OGTT) levels. For the biomarkers and/or blood glucose indicators described herein, efficacy of treatment can determined by quantitating the level of a biomarker or blood glucose indicator in a sample from a subject and determining whether the level of the biomarker or blood glucose indicator has reached or is approaching a threshold level. In some embodiments, a threshold level may correspond to a level of biomarker or blood glucose indicator that is a "normal" (i.e., non-diabetic) value according to standards known in the art. In some embodiments, a threshold level may correspond to a level of biomarker or blood glucose indicator that is a pre-diabetic or diabetic value according to standards known in the art.

In some embodiments, efficacy of treatment is determined by taking a first measurement of one or more of the biomarkers and/or blood glucose indicators in a subject prior to the start of treatment, and comparing the first measurement with secondary measurements of the same biomarker and/or blood glucose indicator in the subject at one or more time points after the onset of treatment, wherein a second measurement that has reached or exceeded a threshold value (either above or below, depending on the biomarker being measured), or is closer to the threshold value than the first measurement is to the threshold value, indicates that the treatment is efficacious. In some embodiments, a second measurement that is at least 10%, at least 20%, at least 30%, at least 40%, at least 50%, at least 60%, at least 70%, at least 80%, at least 90%, or at least 100% or more closer to a threshold value than the first measurement is to the threshold value indicates that the treatment is efficacious. In some embodiments, efficacy of treatment is determined by measuring a biomarker and/or blood glucose indicator in a subject in need of treatment at a time after the onset of treatment, and comparing the value to a measurement of the same biomarker and/or blood glucose indicator in another subject in need of treatment who has not received the treatment, wherein a measurement in the subject being treated that reaches or exceeds the threshold value or is closer to the threshold value than the measurement in the subject not being treated indicates that the treatment is efficacious.

If the biomarker HbA1c is used to measure efficacy of treatment, the threshold level may correspond to "normal" (i.e., non-diabetic) HbA1c levels, for which standards are known in the field, or alternatively the threshold level may correspond to an HbA1c level that is in the pre-diabetic or diabetic range. If the threshold level for HbA1c corresponds to normal HbA1c levels, then the threshold level can be any HbA1c value that is less than 6.0%. If the threshold level for HbA1c corresponds to pre-diabetic HbA1c levels, then the threshold level can be any HbA1c value that is greater than or equal to 6.0% but less than 6.5%. If the threshold level for HbA1c corresponds to diabetic HbA1c levels, then the threshold level can be any HbA1c value that is greater than or equal to 6.5%. In some instances, it may be desirable to set the threshold level to correspond to a normal HbA1c level, while in some instances it may be desirable to set the threshold level to correspond to a HbA1c level that is in the pre-diabetic or diabetic range. For example, in some embodiments, the threshold level for HbA1c is set at about 13%, 12%, 11%, 10%, 9%, 8%, 7%, 6.5%, 6%, 5.5% or 5%, depending on the baseline HbA1c levels of the patient prior to treatment.

Efficacy of treatment can be determined by taking a first measurement of HbA1c in a subject prior to the start of treatment, and comparing the first measurement with a second measurement of HbA1c in the subject at a time after the onset of treatment, wherein a second measurement that is below the set threshold level, or is closer to the set threshold level that the first measurement is to the threshold level, indicates that the treatment is efficacious. As a non-limiting example, if a subject to be treated according to the methods of the present invention has a first HbA1c measurement that is in the diabetic range (i.e., greater than 6.5%), for example 8.0%, in some instances it may be desirable for the HbA1c threshold level for efficacious treatment to be some value less than 6.0% (i.e., in the normal range), in some instances it may be desirable for the HbA1c threshold level for efficacious treatment to be some value greater than or equal to 6.0% but less than 6.5% (i.e., in the pre-diabetic range), and in some instances it may be desirable for the HbA1c threshold level for efficacious treatment to be some value greater than or equal to 6.5% (i.e., in the diabetic range) but less than the value of the subject's first HbA1c measurement (in this example, a value less than 8.0%). In some embodiments, a decrease in HbA1c levels at the second time point measurement of at least 10%, at least 20%, at least 30%, at least 40%, at least 50%, at least 60%, at least 70%, at least 80%, at least 90%, or at least 100%, or more, in comparison to the level at the first time point measurement indicates that the treatment is efficacious.

If the biomarker C-peptide is used to measure efficacy of treatment, in some instances it may be desirable for the threshold level to be set to correspond to a normal (i.e., non-diabetic) C-peptide level (i.e., a threshold level that is between 0.5 and 2.0 ng/ml), or alternatively in some instances it may be desirable for the threshold level to be set to correspond to a C-peptide level that is lower than 0.5 ng/ml or higher than 2.0 ng/ml. As a non-limiting example, if a subject to be treated according to the methods of the present invention has a first C-peptide measurement that is lower than normal levels (i.e., lower than 0.5 ng/ml), for example, 0.25 ng/ml, in some instances it may be desirable for the C-peptide threshold level for efficacious treatment to be some value between 0.5 ng/ml and 2.0 ng/ml (i.e., in the normal range), or in some instances it may be desirable for the C-peptide threshold level for efficacious treatment to be some value less than 0.5 ng/ml but higher than the value of the subject's first C-peptide measurement (in this example, a value greater than 0.25 ng/ml). In some embodiments, an increase in C-peptide levels at the second time point measurement of at least 10%, at least 20%, at least 30%, at least 40%, at least 50%, at least 60%, at least 70%, at least 80%, at least 90%, or at least 100%, or more, in comparison to the level at the first time point measurement indicates that the treatment is efficacious.

If the FPG blood glucose indicator test is used to measure efficacy of treatment, in some instances it may be desirable for the threshold level to be set to correspond to a normal (i.e., non-diabetic) FPG level (i.e., a threshold level that is less than 100 mg/dl), or alternatively the threshold level may correspond to a FPG level that is in the pre-diabetic or diabetic range. If the threshold level for FPG corresponds to pre-diabetic FPG levels, then the threshold level can be any FPG value that is between 100 mg/dl and 125 mg/dl. If the threshold level for FPG corresponds to diabetic FPG levels, then the threshold level can be any FPG value that is greater than 125 mg/dl. In some instances, it may be desirable to set the threshold level to correspond to a normal FPG level, while in some instances it may be desirable to set the threshold level to correspond to a FPG level that is in the pre-diabetic or diabetic range. As a non-limiting example, if a subject to be treated according to the methods of the present invention has a first FPG measurement that is in the diabetic range (i.e., greater than 125 mg/dl), for example 200 mg/dl, in some instances it may be desirable for the FPG threshold level for efficacious treatment to be some value less than 100 mg/dl (i.e., in the normal range), in some instances it may be desirable for the FPG threshold level for efficacious treatment to be some value between 100 mg/dl and 125 mg/dl (i.e., in the pre-diabetic range), and in some instances it may be desirable for the FPG threshold level for efficacious treatment to be some value greater than or equal to 125 mg/dl (i.e., in the diabetic range) but less than the value of the subject's first FPG measurement (in this example, a value less than 200 mg/dl). In some embodiments, a decrease in FPG blood glucose levels at the second time point measurement of at least 10%, at least 20%, at least 30%, at least 40%, at least 50%, at least 60%, at least 70%, at least 80%, at least 90%, or at least 100%, or more, in comparison to the level at the first time point measurement indicates that the treatment is efficacious.

If the OGTT blood glucose indicator test is used to measure efficacy of treatment, in some instances it may be desirable for the threshold level to be set to correspond to a normal (i.e., non-diabetic) OGTT level (i.e., a threshold level that is less than 140 mg/dl), or alternatively the threshold level may correspond to a OGTT level that is in the pre-diabetic or diabetic range. If the threshold level for OGTT corresponds to pre-diabetic OGTT levels, then the threshold level can be any OGTT value that is between 140 mg/dl but less than 200 mg/dl. If the threshold level for OGTT corresponds to diabetic OGTT levels, then the threshold level can be any OGTT value that is greater than 200 mg/dl. In some instances, it may be desirable to set the threshold level to correspond to a normal OGTT level, while in some instances it may be desirable to set the threshold level to correspond to a OGTT level that is in the pre-diabetic or diabetic range. As a non-limiting example, if a subject to be treated according to the methods of the present invention has a first OGTT measurement that is in the diabetic range (i.e., greater than 200 mg/dl), for example 250 mg/dl, in some instances it may be desirable for the OGTT threshold level for efficacious treatment to be some value less than 140 mg/dl (i.e., in the normal range), in some instances it may be desirable for the OGTT threshold level for efficacious treatment to be some value between 140 mg/dl and 200 mg/dl (i.e., in the pre-diabetic range), and in some instances it may be desirable for the OGTT threshold level for efficacious treatment to be some value greater than or equal to 200 mg/dl (i.e., in the diabetic range) but less than the value of the subject's first OGTT measurement (in this example, a value less than 250 mg/dl). In some embodiments, a decrease in OGTT blood glucose levels at the second time point measurement of at least 10%, at least 20%, at least 30%, at least 40%, at least 50%, at least 60%, at least 70%, at least 80%, at least 90%, or at least 100%, or more, in comparison to the level at the first time point measurement indicates that the treatment is efficacious.

Alternatively or additionally, efficacy of treatment may be monitored by determining whether there has been an amelioration of the secondary conditions and symptoms that are associated with the diabetic condition. For example, a subject being treated by the methods of the present invention can be monitored for improvement or reduction in symptoms of retinopathy (e.g., improvement in vision), nephropathy (e.g., improvement in kidney structure or function), neuropathy (e.g., improvement in nerve function), and/or cardiovascular disease (e.g., decreased blood pressure or lower lipid levels).

B. Pharmacological Agents

The pharmacological agents used in the present methods and compositions include the one or more active agents, described in detail below, in any pharmaceutically acceptable form, including any pharmaceutically acceptable salts, pro-drugs, racemic mixtures, conformational and/or optical isomers, crystalline polymorphs and isotopic variants of the one or more pharmacological agents.

1. Telenzepine

The present methods treat diabetes by administering to an individual in need thereof a therapeutic amount of telenzepine, a selective muscarinic receptor $M_1$ antagonist. Muscarinic antagonists are generally reviewed in Chapter 7 of *Goodman and Gilman's The Pharmacological Basis of Therapeutics*, supra, hereby incorporated herein by reference. The structure of telenzepine is shown below.

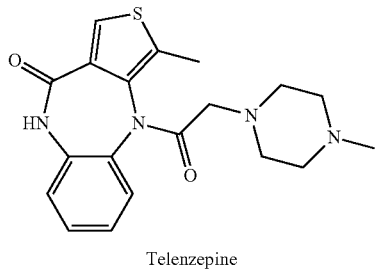 [SMILES: Cc1scc2c1N(C(=O)CN1CCN(C)CC1)c1ccccc1NC2=O]

Telenzepine

Telenzepine (4,9-Dihydro-3-methyl-4-[(4-methyl-1-piperazinyl)acetyl]-10H-thieno[3,4-b][1,5]benzodiazepin-10-one) is commercially available from, for example, Tocris Bioscience (Ellisville, Mo.) and Sigma-Aldrich, Inc. (St. Louis, Mo.) as telenzepine dihydrochloride. Further, the synthesis of telenzepine is disclosed in U.S. Pat. No. 4,381,301, hereby incorporated herein by reference. Telenzepine can be administered in doses from about 0.1 mg per day to about 10 mg per day, for example, about 0.1-10 mg/day, about 0.2-8 mg/day, about 0.3-6 mg/day, about 0.5-5 mg/day, about 1-5 mg/day, or about 1-3 mg/day, or about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg/day. According to U.S. Pat. No. 4,381,301, telenzepine can be administered orally in a daily dose of from about 0.01 to about 5, from 0.05 to 2.5, or from 0.1 to 1.5 mg/kg of body weight, generally in the form of several, for example from 1 to 3, individual administrations in order to achieve the desired results. An individual administration contains the active compound or compounds in an amount of from about 0.01 to about 2.5, from 0.01 to 1.5, or from 0.05 to 0.5, mg/kg of body weight. Similar dosages are used for parenteral, for example intravenous, treatment. Analogs of telenzepine also find use in carrying out the present methods. Chemical analogs and enantiomers of telenzepine are disclosed, for example, in U.S. Pat. Nos. 3,953,430; 4,168,269; 4,172,831; 4,381,301; 5,140,025; and 5,324,832, the disclosures of each of which are hereby incorporated herein by reference in their entirety for all purposes.

In some embodiments a racemic preparation of telenzepine containing a mixture of (+) and (−) enantiomers is administered. In some embodiments, the (+) or (−) enantiomer of telenzepine is administered. Telenzepine exists in two chirally distinct states separated by an activation barrier of 35.5 kcal/mol (Eveleigh et al., *Mol Pharmacol* (1989) 35:477-483; and Schudt et al., *Eur J Pharmacol* (1989) 165: 87-96). The (+) form of telenzepine has potent antimuscarinic activity whereas the (−) form is considerably less active. The selectivity of telenzepine appears to vary at different anatomic sites with the (+) form more effective on cortical receptors by a factor of 400 compared to the (−) isomer; on cardiac receptors the selectivity is less and the (+) form is more potent than the (−) form by a factor of 50 (Eveleigh et al., supra). The two forms interconvert slowly and with a half time of approximately 200 hours at 90 degrees (Eveleigh et al., supra). Multiple studies have affirmed that the two forms have distinct activities (Eltze, *Eur J Pharmacol* (1990) 180:161-168; Eveleigh et al., supra; Feifel et al., *Eur J Pharmacol* (1991) 195:115-123; Kilian et al., *Agents Actions Suppl* 34:131-147; Schudt et al., supra).

2. Sertraline

In one embodiment, an effective amount of sertraline (or its S-enantiomer, Zoloft®) is co-administered. The sertraline S-enantiomer, Zoloft® is commercially available from Pfizer Inc. as sertraline hydrochloride. Further, the synthesis of sertraline and its S-enantiomer are disclosed in U.S. Pat. No. 4,536,518, hereby incorporated herein by reference. For the methods of the present invention, sertraline (or its S-enantiomer, Zoloft®) can be administered in therapeutic doses ranging from about 50-200 mg/day, for example about 50-150 mg/day. For example, sertraline (or its S-enantiomer, Zoloft®) can be administered in a therapeutic dose of about 50, 60, 70, 80, 90, 100, 110, 120, 130, 140, 150, 160, 170, 180, 190, or 200 mg/day. According to U.S. Pat. No. 4,536,518, sertraline (or its S-enantiomer, Zoloft®) can be administered orally or parenterally in a daily dose of from about 0.3 to about 10 mg/kg of body weight, for example in a daily dose of about 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg/kg of body weight. Appropriate therapeutic dosages for sertraline will depend on the chosen route of administration and formulation of the composition, among other factors.

Alternatively, for the methods of the present invention, subtherapeutic dosages of sertraline (or its S-enantiomer, Zoloft®) are administered at doses that are about 75% or less of a full dose for the indicated purposes of sertraline. For example, in the present methods sertraline (or its S-enantiomer, Zoloft®) is administered in amounts that are about 75%, 50%, 30%, 25%, 20%, 10%, 5%, 2%, 1% or less than a full dose. Dosing of sertraline is known in the art and published in standard reference texts commonly consulted by trained clinicians, including for example, *Goodman and Gilman's The Pharmacological Basis of Therapeutics*, $11^{th}$ Edition, 2006, supra, in a Physicians' Desk Reference (PDR), for example, in the $62^{nd}$ (2008) Ed., Thomson PDR, and in the FDA Orange Book. In some embodiments, the subtherapeutic amounts of sertraline (or its S-enantiomer, Zoloft®) are administered orally in doses from about 12.5-50 mg/day, for example, about 12.5, 15, 20, 25, 30, 35, 40, 45, or 50 mg/day.

3. Combinations of Pharmacological Agents

In some embodiments, a method of treating a diabetic condition (e.g., type 1 diabetes, type 2 diabetes, pre-diabetes, chronic hyperglycemia, or metabolic syndrome) comprising co-administering telenzepine and sertraline further comprises administering one or more anti-diabetic agents as described herein. In some embodiments, a combination of telenzepine and sertraline for use in the treatment of a diabetic condition (e.g., type 1 diabetes, type 2 diabetes, pre-diabetes, chronic hyperglycemia, or metabolic syndrome) further comprises one or more anti-diabetic agents as described herein.

4. Anti-Diabetic Agents

The present invention contemplates that the use of telenzepine and sertraline in further combination with other therapeutic agents, particularly those used for treating diabetes, pre-diabetes, hyperglycemia, and/or diabetic complications. Such other therapeutic agents include, but are not limited to, anti-diabetic agents and agents for treating diabetic complications. Those skilled in the art will appreciate that other therapeutic agents discussed below can have multiple therapeutic uses and the listing of an agent in one particular category should not be construed to limit in any way its usefulness in combination therapy within the present invention.

Examples of anti-diabetic agents suitable for use in combination with telenzepine and sertraline include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid-x receptor (RXR) agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, alogliptin, dutogliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), sodium-dependent glucose cotransporter inhibitors (such as dapagliflozin, canagliflozin, tofogliflozin, ipragliflozin, empagliflozin, luseogliflozin, EGT1442, ASP1941, LX4211, remogliflozin, sergliflozin, BI 10773, BI 44847, R-7201, TS-071, compounds described in Washburn, W. N., Expert Opinion on Therapeutic Patents, Vol. 19, No. 11, 2009, pp. 1485-1499, compounds described in U.S. Patent Publication Nos. US2010/0056618 and US2011/0077212, compounds described in WIPO Patent Publication Nos. WO 2011/048112 and WO 2011/051864, and the like), glucokinase activators (such as ARRY-403, piragliatin (R04389620), R00281675, MK-0941, TTP355, GKA50, GKA60, GKM-001, PSN010, PSN-GK1, compounds described in Sarabu, R., et al., *Expert Opinion on Therapeutic Patents*, Vol. 21, No. 1, 2011, pp. 13-33, and the like), protein tyrosine phosphatase-1B inhibitors (such as KR61639, IDD-3, PTP-3848, PTP-112, OC-86839, PNU-177496, compounds described in Vats, R. K., et al., *Current Science*, Vol. 88, No. 2, 25 Jan. 2005, pp. 241-249, and the like), glycogen phosphorylase inhibitors (such as NN-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science*, Vol. 88, No. 2, 25 Jan. 2005, pp. 241-249, and the like), 11 beta-hydroxysteroid dehydrogenase type 1 inhibitors (such as carbenoxolone, INCB13739 and the like), glucagon receptor antagonists (such as BAY-27-9955, NN-2501, NNC-92-1687 and the like), glucagon-like peptide-1 (GLP-1), GLP-1 receptor agonists (such as exenatide, liraglutide, CJC-1131, AVE-0100, AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with telenzepine and sertraline include aldose reductase inhibitors (such as epalrestat, imirestat, tolrestat, minalrestat, ponairestat, zopolrestat, fidarestat, ascorbyl gamolenate, ADN-138, BAL-AR18, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methyl-hydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

5. Isomers

All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers of the therapeutic agents are within the scope of the present invention.

6. Isotopes

The present invention also includes isotopically-labeled variants of the therapeutic agents, wherein one or more atoms are replaced by one or more atoms having specific atomic mass or mass numbers. Isotopically-labeled variants of the therapeutic agents and prodrugs thereof, as well as isotopically-labeled, pharmaceutically acceptable salts of the therapeutic agents and prodrugs thereof, are within the scope of the present invention. In certain circumstances substitution with heavier isotopes, such as deuterium ($^2H$), can provide increased metabolic stability, which offers therapeutic advantages such as increased in vivo half-life or reduced dosage requirements. Isotopically-labeled variants of the therapeutic agents of this invention and prodrugs thereof can generally be prepared according to methods known to those skilled in the art by substituting an isotopically-labeled reagent for a non-isotopically labeled reagent.

C. Administration

1. Duration of Administration

Usually, telenzepine and sertraline (and optionally, one or more additional therapeutic agents administered therewith, for example, anti-diabetic agents or agents for treating diabetic complications) are administered to the individual over an extended period of time. The methods can be carried out for at least 20 days, in some embodiments for at least 40, 60, 80 or 100 days, and in some embodiments for at least 150, 200, 250, 300, 350 days, 1 year or longer. Certain individuals receive the present treatment methods for longer than a year, for example, at least 400, 450, 500, 550, 600, 650, 700, 800, 900, 1000 days. However, individuals can be successfully treated with the present methods for 2 years, 3 years, 4 years or longer.

Usually, subjects treated according to the present invention can exhibit at least 10%, at least 20%, at least 30%, at least 40%, at least 50%, at least 60%, at least 70%, at least 80%, at least 90%, or at least 100% or more reduction or improvement in diabetic conditions, as measured by any of the biomarker or blood glucose indicators described herein (e.g., HbA1c, blood glucose, C-peptide levels) or as measured by the amelioration of the secondary conditions and symptoms that are associated with diabetic conditions.

Treatment can be continued after the biomarkers reach a desired threshold value or stabilize at a desired threshold value.

2. Scheduling

Generally, in practicing the present methods, effective amounts of the $M_1R$-selective antagonist telenzepine are co-administered with the antidepressant sertraline (and optionally one or more additional therapeutic agents, for example, anti-diabetic agents or agents for treating diabetic complications). Co-administered pharmacological agents can be administered together or separately, simultaneously or at different times. When administered, telenzepine and sertraline independently can be administered once, twice, three, four times daily or more or less often, as needed. Preferably, the administered pharmacological agents are administered once daily. Preferably, the administered active agents are administered at the same time or times, for instance as an admixture. One or more of the pharmacological agents can be administered in a sustained-release formulation.

For certain patients, the methods are carried out by concurrently administering telenzepine and sertraline from the initiation of treatment. For certain patients, the methods are carried out by first administering telenzepine, and then subsequently co-administering sertraline. The patient initially can be given telenzepine alone for as long as 3 days, 5 days, 7 days, 10 days, 14 days, 20 days, or 30 days before commencing administration of sertraline.

Telenzepine and sertraline (and optionally one or more additional therapeutic agents, for example, anti-diabetic agents or agents for treating diabetic complications) can be administered prophylactically to prevent undesirable recurrence of diabetic symptoms, or therapeutically to achieve a desired reduction in symptoms of diabetes and maintain such reduction in symptoms of diabetes for a sustained period of time.

3. Routes of Administration

Administration of telenzepine and sertraline (and optionally one or more additional therapeutic agents, for example, anti-diabetic agents or agents for treating diabetic complications) can be achieved in various ways, including oral, buccal, parenteral, including intravenous, intradermal, subcutaneous, intramuscular, transdermal, transmucosal, intranasal, etc., administration. The pharmacologic) agents as described herein can be administered by the same or different routes of administration when co-administered.

In some embodiments, telenzepine, alone or in combination with sertraline (and optionally one or more additional therapeutic agents, for example, anti-diabetic agents or agents for treating diabetic complications), can be administered in a local rather than systemic manner, for example, in a depot or sustained release formulation.

4. Methods of Determining Appropriate Dosages

Administered dosages for telenzepine, sertraline, and the anti-diabetic agents and agents for treating diabetic complications as described herein are in accordance with dosages and scheduling regimens practiced by those of skill in the art. General guidance for appropriate dosages of all pharmacological agents used in the present methods is provided in *Goodman and Gilman's The Pharmacological Basis of Therapeutics,* 11th Edition, 2006, supra, and in a Physicians' Desk Reference (PDR), for example, in the $59^{th}$ (2005) or $60^{th}$ (2006) Eds., Thomson PDR, each of which is hereby incorporated herein by reference. Published dosages for telenzepine and sertraline are for indications distinct from treatments to treat diabetes. In the compositions and methods of the present invention, efficacious dosages of telenzepine and sertraline for practicing the present invention can be equal to or less than (e.g., about 25, 50, 75 or 100%) the dosages published for other indications.

The appropriate dosage of telenzepine, sertraline, and one or more anti-diabetic agents or agents for treating diabetic complications will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

Determination of an effective amount is well within the capability of those skilled in the art, especially in light of the detailed disclosure provided herein. Generally, an efficacious or effective amount of a combination of telenzepine and sertraline is determined by first administering a low dose or small amount of each telenzepine and sertraline, and then incrementally increasing the administered dosages, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 11th Edition, 2006, supra; in a Physicians' Desk Reference (PDR), supra; in *Remington: The Science and Practice of Pharmacy*, $21^{st}$ Ed., 2006, supra; and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

III. Pharmaceutical Compositions

The present invention further provides pharmaceutical compositions comprising a mixture of a therapeutically effective amount of the $M_1R$-selective antagonist telenzepine and the selective serotonin reuptake inhibitor (SSRI) antidepressant sertraline (or its S-enantiomer, Zoloft®). In some embodiments, the pharmaceutical composition further comprises one or more additional therapeutic agents, for example, anti-diabetic agents or agents for treating diabetic complications as described herein.

A combination of telenzepine and sertraline (and optionally one or more additional therapeutic agents, for example, anti-diabetic agents or agents for treating diabetic complications) can be administered to a subject, e.g., a human patient, a domestic animal such as a cat or a dog, independently or together in the form of their pharmaceutically acceptable salts, or in the form of a pharmaceutical composition where the compounds are mixed with suitable carriers or excipient(s) in a therapeutically effective amount, e.g., at doses effective to alleviate, relieve, or reduce the symptoms or conditions of diabetes. In some embodiments, the pharmaceutical composition comprises telenzepine at a dose of about 0.1-10 mg/day, about 0.1-6 mg/day, about 0.3-6 mg/day, about 0.5-5 mg/day, about 1-5 mg/day, or about 1-3 mg/day, or about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg/day. In some embodiments, the pharmaceutical composition comprises sertraline at a dose of about 25-250 mg/day, for example, about 50-250 mg/day, about 50-200 mg/day, or about 50-150 mg/day, or about 50, 60, 70, 80, 90, 100, 110, 120, 130, 140, 150, 160, 170, 180, 190, or 200 mg/day.

A combination of telenzepine and sertraline (and optionally one or more additional therapeutic agents, for example, anti-diabetic agents or agents for treating diabetic complications) can be incorporated into a variety of formulations for therapeutic administration. More particularly, a combination of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Suitable formulations for use in the present invention are found in, for example, in *Remington: The Science and Practice of Pharmacy*, 21$^{st}$ Ed., 2006, supra; *Martindale: The Complete Drug Reference*, Sweetman, 2005, London: Pharmaceutical Press; Niazi, *Handbook of Pharmaceutical Manufacturing Formulations*, 2004, CRC Press; and Gibson, *Pharmaceutical Preformulation and Formulation: A Practical Guide from Candidate Drug Selection to Commercial Dosage Form*, 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one embodiment, a combination of telenzepine and sertraline (and optionally one or more additional therapeutic agents, for example, anti-diabetic agents or agents for treating diabetic complications) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601(2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a combination of telenzepine and sertraline of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a combination of telenzepine and sertraline (and optionally one or more additional therapeutic agents, for example, anti-diabetic agents or agents for treating diabetic complications) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, a combination of telenzepine and sertraline (and optionally one or more additional therapeutic agents, for example, anti-diabetic agents or agents for treating diabetic complications) can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a combination of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in a conventional manner.

In addition to the formulations described previously, a combination of telenzepine and sertraline (and optionally one or more additional therapeutic agents, for example, anti-diabetic agents or agents for treating diabetic complications) of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

IV. Kits

The pharmaceutical compositions of the present invention can be provided in a kits for use in the treatment and prevention of diabetes in subjects in need thereof. In certain embodiments, a kit of the present invention comprises telenzepine and sertraline (and optionally one or more additional therapeutic agents, for example, anti-diabetic agents or agents for treating diabetic complications) in separate formulations. In certain embodiments, the kits comprise telenzepine and sertraline (and optionally one or more additional therapeutic agents, for example, anti-diabetic agents or agents for treating diabetic complications) within the same formulation. In certain embodiments, the kits provide telenzepine and sertraline independently in uniform dosage formulations throughout the course of treatment. In certain embodiments, the kits provide telenzepine and sertraline (and optionally one or more additional therapeutic agents, for example, anti-diabetic agents or agents for treating diabetic complications) independently in graduated dosages over the course of treatment, either increasing or decreasing, but usually increasing to an efficacious dosage level, according to the requirements of an individual. In some embodiments, a kit comprises telenzepine at a dose of about 0.1-10 mg/day, about 0.1-6 mg/day, about 0.3-6 mg/day, about 0.5-5 mg/day, about 1-5 mg/day, or about 1-3 mg/day, or about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg/day. In some embodiments, a kit comprises sertraline at a dose of about 25-250 mg/day, for example, about 50-250 mg/day, about 50-200 mg/day, or about 50-150 mg/day, or about 50, 60, 70, 80, 90, 100, 110, 120, 130, 140, 150, 160, 170, 180, 190, or 200 mg/day.

In one embodiment, the kits comprise one or more pharmaceutical compositions comprising telenzepine and sertraline (or its S-enantiomer, Zoloft®). In one embodiment, the kits comprise one or more pharmaceutical compositions comprising telenzepine, sertraline (or its S-enantiomer, Zoloft®), and one or more additional therapeutic agents, e.g., an anti-diabetic agent or an agent for treating diabetic complications.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a diabetic condition in a subject in need thereof comprising co-administering to the subject telenzepine and sertraline.

2. The method of claim 1, wherein one or both of the telenzepine and sertraline are administered in a therapeutically effective amount.

3. The method of claim 1, wherein one or both of the telenzepine and the sertraline are administered in a sub-therapeutic amount.

4. The method of claim 1, wherein the telenzepine is administered at a dose in the range of about 0.1-6 mg/day.

5. The method of claim 1, wherein the telenzepine is administered at a dose in the range of about 1-3 mg/day.

6. The method of claim 1, wherein the sertraline is administered at a dose in the range of about 50-200 mg/day.

7. The method of claim 1, wherein the sertraline is administered at a dose in the range of about 50-150 mg/day.

8. The method of claim 1, wherein the telenzepine is systemically administered.

9. The method of claim 1, wherein one or both of the telenzepine and the sertraline are administered in a sustained release formulation.

10. The method of claim 1, wherein the telenzepine and the sertraline are administered concurrently.

11. The method of claim 1, wherein the telenzepine and the sertraline are administered sequentially.

12. The method of claim 1, further comprising administering to the subject one or more anti-diabetic agents.

13. The method of claim 1, wherein the subject has type 2 diabetes.

14. The method of claim 1, wherein the subject has metabolic syndrome.

15. The method of claim 1, wherein the subject is not overweight or obese.

16. The method of claim 1, wherein the subject is a human.

17. A method of lowering plasma level of HbA1c in a subject in need thereof comprising co-administering to the subject telenzepine and sertraline.

18. The method of claim 17, wherein the HbA1c level is lowered below a threshold level.

19. The method of claim 17, wherein the HbA1c level is lowered by at least about 5%.

20. The method of claim 17, wherein one or both of the telenzepine and sertraline are administered in a therapeutically effective amount.

21. The method of claim 17, wherein one or both of the telenzepine and the sertraline are administered in a sub-therapeutic amount.

22. The method of claim 17, wherein the telenzepine is administered at a dose in the range of about 0.1-6 mg/day.

23. The method of claim 17, wherein the telenzepine is administered at a dose in the range of about 1-3 mg/day.

24. The method of claim 17, wherein the sertraline is administered at a dose in the range of about 50-200 mg/day.

25. The method of claim 17, wherein the sertraline is administered at a dose in the range of about 50-150 mg/day.

26. The method of claim 17, wherein the telenzepine is systemically administered.

27. The method of claim 17, wherein one or both of the telenzepine and the sertraline are administered in a sustained release formulation.

28. The method of claim 17, wherein the telenzepine and the sertraline are administered concurrently.

29. The method of claim 17, wherein the telenzepine and the sertraline are administered sequentially.

30. The method of claim 17, further comprising administering to the subject one or more anti-diabetic agents.

31. The method of claim 17, wherein the subject has a diabetic condition.

32. The method of claim 31, wherein the subject is pre-diabetic.

33. The method of claim 31, wherein the subject has type 2 diabetes.

34. The method of claim 31, wherein the subject has metabolic syndrome.

35. The method of claim 17, wherein the subject is not overweight or obese.

36. The method of claim 17, wherein the subject is a human.

* * * * *